United States Patent [19]

Zoeller et al.

[11] Patent Number: 5,292,948
[45] Date of Patent: Mar. 8, 1994

[54] CONTINUOUS PROCESS FOR THE PREPARATION OF ACETIC ANHYDRIDE OR MIXTURES OF ACETIC ANHYDRIDE AND ACETIC ACID

[75] Inventors: Joseph R. Zoeller; Charles E. Outlaw; Regina M. Moncier, all of Kingsport, Tenn.

[73] Assignee: Eastman Kodak Company, Rochester, N.Y.

[21] Appl. No.: 68,583

[22] Filed: May 28, 1993

Related U.S. Application Data

[63] Continuation of Ser. No. 630,625, Dec. 20, 1990, abandoned.

[51] Int. Cl.$^5$ .................. C07C 51/56; C07C 51/12; C07C 51/573
[52] U.S. Cl. .................. 562/891; 562/893; 562/898
[58] Field of Search .................. 562/891, 893, 898

[56] References Cited

U.S. PATENT DOCUMENTS

| | | | |
|---|---|---|---|
| 4,046,807 | 9/1977 | Kuckertz. | |
| 4,115,444 | 9/1978 | Rizkalla | 260/549 |
| 4,132,734 | 1/1979 | Singleton | 562/522 |
| 4,252,748 | 2/1981 | Hoch et al. | 568/411 |
| 4,358,411 | 11/1982 | Porcelli et al. | 260/546 |
| 4,534,912 | 8/1985 | Cook | 260/549 |

FOREIGN PATENT DOCUMENTS

| | | | |
|---|---|---|---|
| 0070783 | 1/1983 | European Pat. Off. | 51/56 |
| 0098689 | 1/1984 | European Pat. Off. | 51/54 |
| 384652 | 8/1989 | European Pat. Off. | |

Primary Examiner—José G. Dees
Assistant Examiner—Barbara S. Frazier
Attorney, Agent, or Firm—J. Frederick Thomsen; William P. Heath, Jr.

[57] ABSTRACT

Disclosed is a continuous process for the preparation of acetic anhydride which comprises carbonylating a mixture comprising (i) methyl iodide and (ii) methyl acetate and/or dimethyl ether in the presence of a rhodium catalyst and a promoter wherein the concentration of mesityl oxide in the carbonylation mixture is suppressed by the presence therein of at least 100 ppm of dissolved ferrous and/or cobaltous ion.

11 Claims, No Drawings

CONTINUOUS PROCESS FOR THE PREPARATION OF ACETIC ANHYDRIDE OR MIXTURES OF ACETIC ANHYDRIDE AND ACETIC ACID

This application is a continuation of application Ser. No. 07/630,625, filed Dec. 20, 1990, now abandoned.

This invention pertains to the manufacture of acetic anhydride by continuous carbonylation processes. More specifically, this invention pertains to the preparation of acetic anhydride and acetic anhydride/acetic acid mixtures by continuous carbonylation processes wherein the carbonylation rate is increased, tar formation is decreased, and the acetic anhydride, or mixture of acetic anhydride and acetic acid, produced contains lower concentrations of reducing substances and possesses improved color.

The preparation of acetic anhydride by contacting a mixture comprising methyl iodide and methyl acetate and/or dimethyl ether with carbon monoxide in the presence of a rhodium catalyst has been reported extensively in the patent literature. See, for example, U.S. Pat. Nos. 3,927,078; 4,046,807; 4,115,444; 4,374,070; 4,430,273; and 4,559,183 and European Patents 8396; 87,869; and 87,870. These patents disclose that the reaction rate can be increased if the catalyst system includes a promoter such as certain amines and quaternary ammonium compounds, phosphines and phosphonium compounds and inorganic compounds such as lithium compounds. The crude or partially-refined product obtained from such acetic anhydride processes typically comprises a mixture of acetic anhydride and acetic acid as a result of the use of acetic acid as a process solvent and/or the coproduction of acetic acid by including methanol and/or water in the feed to the carbonylation reactor.

The acetic anhydride and acetic acid obtained from the carbonylation processes referred to above must be purified and refined to meet the purity requirements of users thereof. One of the most important purity specifications which is especially difficult to achieve is the concentration of "reducing substances". See, for example, Published European Patent Application 372,993. Typical specifications require a permanganate reducing substances test value (permanganate time) of at least 30 minutes according to a modification of the Substances Reducing Permanganate Test, American Chemical Society Specifications published in Reagent Chemicals, 6th Ed., American Chemical Society, Washington, D.C., pp. 66 and 68.

It is known (U.S. Pat. Nos. 4,252,748; 4,444,624; and 4,717,454) that acetone is formed during the manufacture of acetic anhydride by continuous carbonylation processes. Typically, the acetone formed accumulates in the carbonylation reactor of the acetic anhydride production system to a maximum level of about 4.0 to 6.0 weight percent, based on the total weight of the contents of the carbonylation reactor. It is believed that acetone is consumed in the reactor to produce process "tars" and other undesirable by-products of the carbonylation process. Removal of acetone is not essential to the operation of the production system and the cost of its separation and purification is not justified by the value of the relatively small amount of acetone formed.

We have found that mesityl oxide (4-methyl-3-buten-2-one) is the primary component of the undesirable reducing substances formed during the continuous operation of the carbonylation processes described in prior art cited above. It is believed that mesityl oxide is formed from acetone according to the reaction:

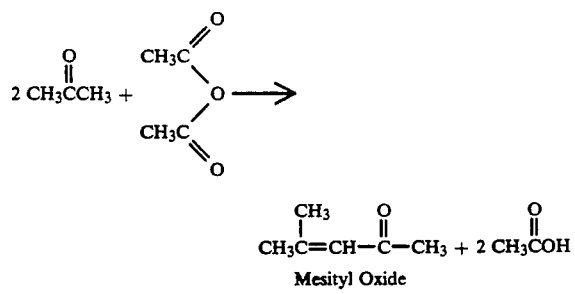

Mesityl oxide is extremely difficult to separate from mixtures of acetic acid and acetic anhydride by conventional, industrial distillation equipment since its boiling point (130° C.) is midway between the boiling points of acetic acid (118° C.), and acetic anhydride (140° C.). The presence of mesityl oxide in the carbonylation reactor also appears to have a negative effect on carbonylation rate since its decomposition in accordance with our invention is accompanied by improved carbonylation rates.

We also have observed the presence of 2,4-pentanedione (acetylacetone) in the carbonylation reactor. This compound also may retard reaction rates, possibly by the formation of another $\alpha,\beta$-unsaturated ketone from the acetylation of its enol isomer, e.g.:

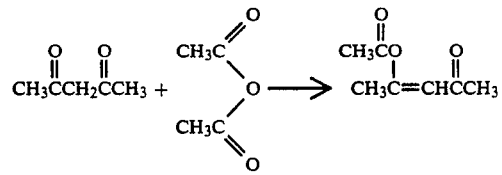

or by direct coordination via the enolate anion. The above $\alpha,\beta$-unsaturated ketone (4-acetoxy-3-buten-2-one) also may retard the carbonylation rate.

We have discovered that the concentration of $\alpha,\beta$-unsaturated ketones, e.g., mesityl oxide, including compounds capable of generating $\alpha,\beta$-unsaturated ketones, e.g., 2,4-pentanedione, formed during the continuous carbonylation reaction mixture can be reduced substantially by including in the reaction mixture at least 85, usually at least 100 parts, per million (ppm) of dissolved ferrous (Fe II) and/or cobaltous (Co II) ion. Thus, the present invention provides a continuous process for the preparation of acetic anhydride by the carbonylation of a mixture comprising (i) methyl iodide and (ii) methyl acetate and/or dimethyl ether in the presence of a rhodium catalyst and a promoter wherein the concentration of $\alpha,\beta$-unsaturated ketones such as mesityl oxide in the carbonylation mixture is suppressed by the presence therein of at least 85 ppm of dissolved ferrous and/or cobaltous ion.

The presence of iron and/or cobalt ions in the carbonylation process provides a plurality of advantages. First, the reducing substances content of the carbonylation product, i.e., acetic anhydride or acetic anhydride/acetic acid mixture, is reduced substantially, e.g., at least 20%. Concentrations of reducing substances may be expressed as permanganate time, as described hereinabove, or as milliequivalent potassium permanganate consumed per 100 mL of acetic anhydride. Normally, the acetic anhydride and acetic acid products are tested for reducing substances after the carbonylation product has been refined in a distillation train to separate the high boiling fraction of the carbonylation reactor effluent into its various components including acetic anhydride, acetic acid and by-products such as ethylidene diacetate.

A second advantage of our invention consists of an improvement in the carbonylation rate which permits the use of lower concentrations of the rhodium catalyst and/or an increase in the carbonylation rate, i.e., rate of acetic anhydride production. As mentioned hereinabove, decomposition of $\alpha,\beta$-unsaturated ketones improves the rate of carbonylation and thus the rate of production. Other advantages resulting from the suppression of mesityl oxide according to our invention include a reduction in the amount of tars produced and an improvement in the color of the product or products of the carbonylation process.

The process of the present invention is an improvement of the rhodium-catalyzed, carbonylation processes described in the literature such as the patent publications referred to above. Thus, our novel process may be carried out by continuously feeding to a carbonylation zone a mixture comprising (i) methyl iodide, (ii) methyl acetate and/or dimethyl ether and (iii) a promoter while maintaining in the carbonylation zone a catalytic amount of a rhodium catalyst and at least 100 ppm of dissolved ferrous and/or cobaltous ion. The feed to the carbonylation zone also may include (1) acetic acid as a process solvent and/or (2) methanol and/or water to co-produce acetic anhydride and acetic acid as described in Published European Patent Applications 87,869 and 87,870. When using a liquid take-off reactor system, the feed also will include the rhodium catalyst, the promoter and an iron and/or cobalt compound. The rhodium concentration in the carbonylation zone mixture may be from about 250 to 1300 ppm with concentrations of about 400 to 1000 ppm being typically used. The carbonylation zone may comprise one or more pressure vessels which may be provided with means for agitation.

The carbonylation zone is maintained at elevated temperature and pressure such as about 100 to 300° C. and about 21.7 to 276.7 bars absolute (about 300 to 4000 pounds per square inch gauge—psig) although temperatures and pressures in the range of about 175 to 220° C. and 35.5 to 104.4 bars absolute (about 500 to 1500 psig) are more common. The gas fed to the carbonylation zone may consist of essentially carbon monoxide or a mixture of carbon monoxide and hydrogen, e.g., a mixture of carbon monoxide and up to about 7 volume percent hydrogen.

An effluent is continuously removed from the carbonylation zone and separated into a major fraction comprising methyl iodide, methyl acetate and/or dimethyl ether, acetic acid and acetic anhydride and a minor fraction comprising a solution of catalyst components and a ferrous and/or cobaltous compound in a mixture of acetic acid and acetic anhydride. The minor fraction is recycled to the carbonylation zone and the major fraction is separated by a series of distillations into its component parts.

The promoter may be (1) an inorganic iodide salt such as lithium iodide or an iodide salt of a quaternary organophosphorus or organonitrogen compound or (2) an inorganic compound or an organophosphorus or organonitrogen compound which forms an iodide salt in the carbonylation zone. The organophosphorus or organonitrogen iodides may be selected from phosphonium iodides, ammonium iodides and heterocyclic aromatic compounds in which at least one ring hetero atom is a quaternary nitrogen atom. Examples of such phosphorus-and nitrogen-containing iodides include tetra(hydro-carbyl)phosphonium iodides such as tributyl(methyl)phosphonium iodide, tetrabutylphosphonium iodide, tetra-octylphosphonium iodide, triphenyl(methyl)phosphonium iodide, tetraphenylphosphonium iodide and the like; tetra(hydrocarbyl)ammonium iodides such as tetrabutylammonium iodide and tributyl(methyl)ammonium iodide; and heterocyclic aromatic compounds such as N-methylpyridinium iodide, N,N'-dimethylimidazolium iodide, N-methyl-3-picolinium iodide, N-methyl-2,4-litidinium iodide, N-methyl-2,4-lutidinium iodide and N-methylquinolinium iodide. The preferred iodide salt promoters comprise lithium iodide and tetraalkylphosphonium iodides, triphenyl(alkyl)phosphonium iodides, tetraalkylammonium iodides and N,N'-dialkylimidazolium iodides wherein the alkyl groups contain up to about 8 carbon atoms.

A portion or all of the promoter compound may be fed as a compound which forms an iodide salt in the carbonylation zone. Thus, the promoter compounds may be fed initially in the form of their corresponding acetates, hydroxides, chlorides or bromides or the phosphorus-and nitrogen-containing promoters may be fed as compounds in which the phosphorus or nitrogen atoms are trivalent, e.g., tributylphosphine, tributylamine, pyridine, imidazole, N-methylimidazole and the like, which are quaternized by the methyl iodide present in the carbonylation zone.

The amount of the iodide salt promoter present in the carbonylation zone can be varied substantially depending on a variety of factors, especially on the particular promoter used. For example, the concentration of lithium iodide in the reaction mixture may range from about 175 to 5000 ppm Li, preferably about 1500 to 3700 ppm Li, whereas the phosphorus-and nitrogen-containing promoters may be present in concentrations of about 0.5 to 25 weight percent, calculated as their iodide salts and based on the total weight of the reaction mixture, i.e., the contents of the carbonylation zone. The amounts of other materials, e.g., acetic acid, acetic anhydride, methyl iodide, methyl acetate and/or dimethyl ether present in the reaction mixture vary substantially depending, for example, on the carbonylation rate, residence time and concentrations of the iodide salt promoter and acetic acid solvent.

The particular iron or cobalt compound fed to the carbonylation system is not critical so long as it provides a concentration of at least 100 ppm dissolved ferrous and/or cobalt ion in the reaction. Examples of iron and cobalt compounds which may be used include ferrous bromide, ferrous chloride, ferrous iodide, ferrous sulfate, ferrous salts of carboxylic acids such as ferrous acetate, ferrous oxalate, cobaltous chloride, cobaltous bromide, cobaltous carbonate, cobaltous iodide, cobaltous carbonate, cobaltous hydroxide and cobaltous salts of carboxylic acids such as cobaltous formate, cobaltous acetate and cobaltous citrate. It is believed that the dissolved ferrous and/or cobalt ion exists in the carbonylation reaction mixture as acetate and/or iodide salts.

The upper limit on the concentration of the iron and cobalt ion employed according to our invention is limited primarily by the solubility of the ferrous and cobaltous compounds in the reaction mixture. In the continuous process set forth in Example 3, the upper limit on the concentration of ferrous and/or cobaltous ion normally is about 300 ppm. However, in processes in which a co-solvent is used or in which acetic acid constitutes a larger portion of the reaction mixture, higher concentrations, e.g., 500 ppm, of ferrous and/or cobalt ion may be used. The preferred concentration of dissolved ferrous and/or cobaltous ion is in the range of about 120 to 300 ppm. The presence of 120 to 300 ppm dissolved ferrous ion is especially preferred.

The process of our invention suppresses or decreases the concentration of $\alpha,\beta$-unsaturated compounds, particularly mesityl oxide, in the acetic anhydride and acetic acid removed from the carbonylation zone but does not eliminate reducing substances entirely. We have found that the advantages, set forth hereinabove, provided by our process are the most pronounced when the acetone in the carbonylation zone is maintained at a concentration of less than about 4, preferably at about 2 to 3, weight percent based on the total weight of the carbonylation zone reaction mixture. These acetone concentrations may be achieved by known means such as by the processes described in U.S. Pat. Nos. 4,252,748, 4,444,624 and 4,717,454. As is shown in Example 3 and Comparative Example 7 hereof, lowering the acetone concentration usually results in a lowering of reducing substances, particularly mesityl oxide, in the refined acetic anhydride product and also gives improved carbonylation rates and lower tar production rates.

A particularly useful technique for lowering acetone to the above-stated concentrations comprises the steps of:
(1) obtaining from the acetic anhydride production system described herein a low-boiling stream comprising methyl acetate, methyl iodide, acetic acid and acetone;
(2) distilling the stream of Step (1) to obtain:
   (a) an overhead stream comprising methyl acetate, methyl iodide and acetone; and
   (b) an underflow stream comprising methyl acetate, methyl iodide, acetone and essentially all of the acetic acid;
(3) extracting the Step (2) (a) stream with water to obtain:
   (a) a methyl iodide phase containing methyl acetate; and
   (b) an aqueous phase containing methyl acetate, methyl iodide and acetone; and
(4) distilling the aqueous phase to obtain:
   (a) a vapor phase comprising methyl acetate, methyl iodide and minor amounts of acetone and water; and
   (b) an aqueous stream containing methyl acetate and acetone.

In this preferred acetone removal system, streams 2(b), (a) and 4(a) are recycled, directly or indirectly, to the carbonylation zone and stream 4(b) is removed from the production system.

The process provided by our invention is further illustrated by the following examples.

REFERENCE EXAMPLES 1-14

These reference examples demonstrate the ability of iron and cobalt compounds to deplete or decompose mesityl oxide present in mixtures of acetic anhydride and acetic acid. In Reference Example 1, a mixture of 50 g acetic anhydride and 50 g acetic anhydride to which mesityl oxide was added was heated at reflux for 3 hours. In Reference Examples 2-9, the procedure was repeated except that a transition metal compound and an iodide salt promoter or a precursor of an iodide salt promoter were added to the mesityl oxide-containing mixture of acetic anhydride and acetic acid prior to refluxing for 3 hours. In Reference Examples 10-14, the only additional compound used was an iodide salt promoter. The additional compounds and the amounts thereof used in Reference Examples 2-14 were:

| Reference Example 2: | 0.275 g ferrous iodide |
| | 1.480 g lithium acetate dihydrate |
| Reference Example 3: | 0.157 g cobaltous acetate tetrahydrate |
| | 0.238 g lithium iodide |
| Reference Example 4: | 0.157 g nickelous iodide |
| | 1.480 g lithium acetate dihydrate |
| Reference Example 5: | 0.271 g chromium (II) iodide |
| | 1.480 g lithium acetate dihydrate |
| Reference Example 6: | 0.154 g ferrous acetate |
| | 3.360 g N,N'-dimethylimidazolium iodide |
| Reference Example 7: | 0.154 g ferrous acetate |
| | 5.400 g tetrabutylammonium iodide |
| Reference Example 8: | 0.154 g ferrous acetate |
| | 5.860 g triphenyl(methyl)phosphonium iodide |
| Reference Example 9: | 0.154 g ferrous acetate |
| | 5.790 g tetrabutylphosphonium iodide |
| Reference Example 10: | 0.238 g lithium iodide |
| Reference Example 11: | 3.360 g N,N'-dimethylimidazolium iodide |
| Reference Example 12: | 5.400 g tetrabutylammonium iodide |
| Reference Example 13: | 5.860 g triphenyl(methyl)phosphonium iodide |
| Reference Example 14: | 5.790 g tetrabutylphosphonium iodide |

Each of the mixtures of Reference Examples 1-14 was analyzed before and after the 3-hour reflux period. The mesityl oxide concentration (in ppm) of each mixture prior to heating (Initial) and after heating (Final) and the weight percent of mesityl oxide depleted from each mixture are shown in Table I.

TABLE I

| | Mesityl Oxide Conc. | | |
|---|---|---|---|
| Example | Initial | Final | Mesityl Oxide Depleted |
| R-1 | 294 | 266 | 10% |
| R-2 | 368 | 0 | 100% |
| R-3 | 323 | 32 | 90% |
| R-4 | 378 | 196 | 48% |
| R-5 | 375 | 300 | 20% |
| R-6 | 264 | 48 | 82% |
| R-7 | 340 | 175 | 49% |
| R-8 | 299 | 98 | 63% |
| R-9 | 272 | 137 | 50% |
| R-10 | 304 | 284 | 7% |
| R-11 | 245 | 245 | 0% |
| R-12 | 314 | 314 | 0% |
| R-13 | 274 | 254 | 7% |
| R-14 | 286 | 256 | 10% |

Reference Examples 2, 3 and 6-9 demonstrate the capability of a combination of (1) ferrous or cobaltous ion and (2) a promoter to deplete mesityl oxide from mixtures of acetic anhydride and acetic acid. Reference Examples 4 and 5 show that other transition metal salts (nickel acetate and chromium acetate) are substantially less effective in depleting mesityl oxide. Reference Examples 10-14 establish that little, if any, mesityl oxide decomposition occurs in the absence of a transition metal salt.

REFERENCE EXAMPLE 15

To a solution of 50 g acetic acid and 50 g acetic anhydride containing 367 ppm mesityl oxide and 60 ppm 2,4-pentanedione was added 0.154 g ferrous acetate and 0.238 g lithium iodide. The resulting solution was heated at reflux for 3 hours and then analyzed for mesityl oxide and 2,4-pentanedione. The presence of neither mesityl oxide nor 2,4-pentanedione could be detected.

EXAMPLES 1 AND 2 AND COMPARATIVE EXAMPLES 1-6

In these examples acetic anhydride was produced by carbonylating methyl acetate in a 1 liter, stirred autoclave which was constructed of Hastelloy B alloy and equipped with a high pressure condenser and a liquid sampling loop. After the addition of the feed materials, the autoclave was sealed and flushed with nitrogen. The autoclave was pressurized to 28.6 bars absolute (about 400 psig) with a gas consisting of 5 volume percent hydrogen and 95 volume percent carbon monoxide and a gas purge rate of 2.0 moles per hour was established through the autoclave. The contents of the autoclave were heated to 190° C. at which point the pressure was adjusted to 52.7 bars absolute (about 750 psig) using 5:95 hydrogen/carbon monoxide. The temperature and pressure were maintained for 3 hours at 190° C. and 52.7 bars absolute with 5:95 hydrogen/carbon monoxide with a gas flow through the autoclave during the experiment. Liquid samples were removed (1) when the 52.7 bar reaction pressure was first achieved and (2) at the end of the 3-hour reaction period and the samples were analyzed for acetic anhydride content. The acetic anhydride present in sample (1) was subtracted from that present in sample (2) to give a Net Acetic Anhydride Produced value.

COMPARATIVE EXAMPLE 1

The feed materials charged to the autoclave were:

| Methyl acetate | 676.50 g (9.14 moles) |
| --- | --- |
| Methyl iodide | 128.25 g (0.96 moles) |
| Acetic acid | 220.50 g |
| Rhodium trichloride trihydrate | 0.62 g (232 ppm Rh) |
| N,N'-dimethylimidazolium iodide | 42.60 g |

The net Acetic Anhydride Produced was 4.2 moles.

COMPARATIVE EXAMPLE 2

The feed materials charged to the autoclave were:

| Methyl acetate | 676.50 g (9.14 moles) |
| --- | --- |
| Methyl iodide | 128.25 g (0.96 moles) |
| Acetic acid | 220.50 g |
| Rhodium trichloride trihydrate | 0.62 g (232 ppm Rh) |
| N,N'-dimethylimidazolium iodide | 42.60 g |
| Ferrous acetate | 1.10 g (309 ppm Fe) |

The Net Acetic Anhydride Produced was 4.2 moles.

COMPARATIVE EXAMPLE 3

The feed materials charged to the autoclave were:

| Methyl acetate | 676.50 g (9.14 moles) |
| --- | --- |
| Methyl iodide | 128.25 g (0.96 moles) |
| Acetic acid | 220.50 g |
| Rhodium trichloride trihydrate | 0.62 g (228_ ppm Rh) |
| N,N'-dimethylimidazolium iodide | 42.60 g |
| Mesityl oxide | 20.00 g |

The Net Acetic Anhydride Produced was 2.0 moles.

EXAMPLE 1

The feed materials charged to the autoclave were:

| Methyl acetate | 676.50 g (9.14 moles) |
| --- | --- |
| Methyl iodide | 128.25 g (0.96 moles) |
| Acetic acid | 220.50 g |
| Rhodium trichloride trihydrate | 0.62 g (228 ppm Rh) |
| N,N'-dimethylimidazolium iodide | 42.60 g |
| Mesityl oxide | 20.00 g |
| Ferrous acetate | 1.10 g (309 ppm Fe) |

The Net Acetic Anhydride Produced was 3.6 moles.

COMPARATIVE EXAMPLE 4

The feed materials charged to the autoclave were:

| Methyl acetate | 676.50 g (9.14 moles) |
| --- | --- |
| Methyl iodide | 128.25 g (0.96 moles) |
| Acetic acid | 220.50 g |
| Rhodium trichloride trihydrate | 0.62 g (226 ppm Rh) |
| Tetrabutylphosphonium iodide | 73.30 g |

The Net Acetic Anhydride Produced was 3.0 moles.

COMPARATIVE EXAMPLE 3

The feed materials charged to the autoclave were:

| Methyl acetate | 676.50 g (9.14 moles) |
| --- | --- |
| Methyl iodide | 128.25 g (0.96 moles) |
| Acetic acid | 220.50 g |
| Rhodium trichloride trihydrate | 0.62 g (226 ppm Rh) |
| Tetrabutylphosphonium iodide | 73.30 g |
| Ferrous acetate | 1.10 g (301 ppm Fe) |

The Net Acetic Anhydride Produced was 3.1 moles.

COMPARATIVE EXAMPLE 6

The feed materials charged to the autoclave were:

| Methyl acetate | 676.50 g (9.14 moles) |
| --- | --- |
| Methyl iodide | 128.25 g (0.96 moles) |
| Acetic acid | 220.50 g |
| Rhodium trichloride trihydrate | 0.62 g (222 ppm Rh) |
| Tetrabutylphosphonium iodide | 73.30 g |
| Mesityl oxide | 20.00 g |

The Net Acetic Anhydride Produced was pb 2.8 pl moles.

EXAMPLE 2

The feed materials charged to the autoclave were:

| Methyl acetate | 676.50 g (9.14 moles) |
| --- | --- |
| Methyl iodide | 128.25 g (0.96 moles) |
| Acetic acid | 220.50 g |
| Rhodium trichloride trihydrate | 0.62 g (222 ppm Rh) |
| Tetrabutylphosphonium iodide | 73.30 g |
| Mesityl oxide | 20.00 g |

| -continued | |
|---|---|
| Ferrous acetate | 1.10 g (301 ppm Fe) |

The Net Acetic Anhydride Produced was 3.0 moles.

By the addition of mesityl oxide in Examples 1 and 2 and Comparative Examples 3 and 6, those batch experiments simulate the problems encountered in continuous operation wherein both acetone and mesityl oxide are produced and build to significant levels. Examples 1 and 2 and Comparative Examples 1–6 show that (1) mesityl oxide appears to inhibit the carbonylation reaction, (2) dissolved ferrous ion overcomes the inhibitory effect, presumably by decomposing mesityl oxide and (3) in the absence of mesityl oxide, ferrous ion has little, if any, effect on carbonylation rate.

EXAMPLE 3 AND COMPARATIVE EXAMPLE 7

These examples were carried out over a 6 month period of time in a commercial acetic anhydride manufacturing facility using the process described in Example 1 of U.S. Pat. No. 4,374,070 and in the Journal of Chemical Education, 63, 206 (1986). Over the course of these examples the concentrations of rhodium, lithium and iron in the carbonylation reactor varied from 500 to 780 ppm Rh, 1150 to 2020 ppm Li and 69 to 156 ppm Fe. In each example, the water-extraction, acetone removal process described hereinabove was used to lower the acetone concentration in the carbonylation reactor from approximately 4.5 weight percent to 2.5 weight percent. In Comparative Example 7 the average iron concentration was below 100 ppm whereas in Example 3 the average iron concentration was maintained above 100 ppm. The series of distillation columns constituting the product refining equipment and the operation thereof was the same in both examples.

During the commercial operation constituting both examples, approximately every 8 hours samples of the reactor contents were analyzed for rhodium, lithium, iron (dissolved ferrous ion) and acetone and the refined acetic anhydride was tested for reducing substances and evaluated for color. The amounts of acetic anhydride and tar produced were determined periodically.

The results obtained in Example 3 and Comparative Example 7 are shown in Tables II and III, respectively. These tables show the average iron (ferrous ion) concentration (Iron, ppm) for different ranges of acetone concentration as acetone was removed from the production system as described herein. The values given for Acetone Conc. are weight percent acetone based on the total weight of the reaction mixture. Tar Formation Rate is:

$$\frac{\text{kilograms tar produced}}{\text{million kilograms acetic anhydride produced}}$$

as determined by the amount of tar purged from the acetic anhydride production facility, Reducing Substances are milliequivalents of potassium permanganate consumed in 30 minutes per 100 mL refined acetic anhydride determined spectrophotometrically and Color is the value obtained according to ASTM D 1209-84 for the refined acetic anhydride. The Relative Reaction Rate values were determined by (1) dividing the average moles of carbon monoxide consumed per hour for each acetone concentration range by the parts per million rhodium present and (2) dividing each value thus obtained by the lowest value obtained which was the carbonylation rate that occurred in Comparative Example 2 at an acetone concentration of 3.8 to 4.1 weight percent.

TABLE II

| Acetone Conc. | Iron Conc. | Relative Reaction Rate | Reducing Substances | Tar Formation Rate | Color |
|---|---|---|---|---|---|
| 4.2–4.5 | 138 | 1.074 | 0.43 | 620 | 8.2 |
| 3.8–4.1 | 134 | 1.072 | 0.42 | 480 | 6.9 |
| 3.4–3.7 | 121 | 1.122 | 0.37 | 440 | 7.9 |
| 2.5–2.9 | 134 | 1.146 | 0.20 | 300 | 7.1 |

TABLE III

| Acetone Conc. | Iron Conc. | Relative Reaction Rate | Reducing Substances | Tar Formation Rate | Color |
|---|---|---|---|---|---|
| 4.2–4.5 | 86 | 1.045 | 0.52 | 670 | 8.7 |
| 3.8–4.1 | 76 | 1.000 | 0.61 | 810 | 12.6 |
| 3.4–3.7 | 85 | 1.013 | 0.45 | 550 | 10.5 |
| 2.5–2.9 | 95 | 1.085 | 0.29 | 450 | 7.8 |

The data reported in Tables II and III establish that iron has a significant, favorable effect on (1) carbonylation rate, (2) levels of reducing substances in the acetic anhydride produced, (3) tar formation rate and (4) the color of the acetic anhydride. The data further establish that the use of iron in combination with lower levels of acetone enhances those favorable effects.

The invention has been described in detail with particular reference to preferred embodiments thereof, but it will be understood that variations and modifications can be effected within the spirit and scope of the invention.

We claim

1. Continuous process for the preparation of acetic anhydride which comprises carbonylating a mixture comprising (i) methyl iodide and (ii) methyl acetate and/or dimethyl ether in the presence of a rhodium catalyst and a promoter wherein the concentration of mesityl oxide in the carbonylation mixture is suppressed by the presence therein of about 100 to 500 ppm of dissolved ferrous and/or cobaltous ion.

2. Process according to claim 1 wherein carbon monoxide is contacted with a mixture comprising (i) methyl iodide and (ii) methyl acetate in the presence of a rhodium catalyst and a promoter selected from lithium iodide, an iodide salt of a quaternary organophosphorus or organonitrogen compound and a lithium compound or an organophosphorus or organo-nitrogen compound which forms an iodide salt during the process.

3. Process according to claim 1 wherein the mixture contains less than 4 weight percent acetone.

4. Continuous process for the preparation of acetic anhydride which comprises carbonylating a mixture comprising (i) methyl iodide and (ii) methyl acetate in the presence of a rhodium catalyst and a promoter selected from lithium iodide, phosphonium iodides, ammonium iodides and heterocyclic aromatic iodides in which at least one ring hetero atom is a quaternary nitrogen atom wherein the concentration of mesityl oxide in the carbonylation mixture is suppressed by the presence therein of about 120 to 300 ppm of dissolved ferrous and/or cobaltous ion.

5. Process according to claim, 4 which comprises contacting carbon monoxide with a mixture comprising (i) methyl iodide, (ii) methyl acetate and (iii) acetic acid in the presence of a rhodium catalyst and a promoter selected from lithium iodide and tetraalkyl-phosphonium iodides, triphenyl(alkyl)phosphonium iodides, tetraalkylammonium iodides and N,N'-dialkylimidazolium iodides wherein the alkyl groups contain up to about 8 carbon atoms wherein the concentration of mesityl oxide in the carbonylation mixture is suppressed by the presence therein of about 120 to 300 ppm of dissolved ferrous ion.

6. Continuous process for the preparation of acetic anhydride which comprises carbonylating a mixture comprising (i) methyl iodide and (ii) methyl acetate in the presence of a rhodium catalyst and a promoter selected from lithium iodide, phosphonium iodides, ammonium iodides and heterocyclic aromatic iodides in which at least one ring hetero atom is a quaternary nitrogen atom wherein the concentration of mesityl oxide in the carbonylation mixture is suppressed by the presence therein of about 120 to 300 ppm of dissolved ferrous and/or cobaltous ion and the mixture contains less than 3 weight percent acetone.

7. Process according to claim 6 which comprises contacting carbon monoxide with a mixture comprising (i) methyl iodide, (ii) methyl acetate and (iii) acetic acid in the presence of a rhodium catalyst and a promoter selected from lithium iodide and tetraalkyl-phosphonium iodides, triphenyl(alkyl)phosphonium iodides, tetraalkylammonium iodides and N,N'-dialkylimidazolium iodides wherein the alkyl groups contain up to about 8 carbon atoms wherein the concentration of mesityl oxide in the carbonylation mixture is suppressed by the presence therein of about 120 to 300 ppm of dissolved ferrous ion and the mixture contains less than 3 weight percent acetone.

8. Continuous process for the preparation of acetic anhydride which comprises carbonylating a mixture comprising (i) methyl iodide and (ii) methyl acetate and/or dimethyl ether in the presence of a rhodium catalyst and lithium iodide promoter wherein the concentration of mesityl oxide in the carbonylation mixture is suppressed by the presence therein of about 100 to 500 ppm of dissolved ferrous and/or cobaltous ion.

9. Continuous process for the preparation of acetic anhydride which comprises carbonylating a mixture comprising (i) methyl iodide and (ii) methyl acetate in the presence of a rhodium catalyst and lithium iodide promoter wherein the concentration of mesityl oxide in the carbonylation mixture is suppressed by the presence therein of about 120 to 300 ppm of dissolved ferrous and/or cobaltous ion.

10. Process according to claim 9 which comprises contacting carbon monoxide with a mixture comprising (i) methyl iodide, (ii) methyl acetate and (iii) acetic acid in the presence of a rhodium catalyst and lithium iodide promoter wherein the concentration of mesityl oxide in the carbonylation mixture is suppressed by the presence therein of about 120 to 300 ppm of dissolved ferrous ion and the mixture contains less than 3 weight percent acetone.

11. Continuous process for the preparation of acetic anhydride which comprises carbonylating a mixture comprising (i) methyl iodide and (ii) methyl acetate and/or dimethyl ether in the presence of a rhodium catalyst and a promoter, wherein the concentration of mesityl oxide is reduced in the carbonylation mixture by the presence therein of about 100 to 500 ppm of dissolved ferrous and/or cobaltous ion.

* * * * *